(12) United States Patent
März et al.

(10) Patent No.: US 10,481,000 B2
(45) Date of Patent: Nov. 19, 2019

(54) APPARATUS AND METHOD FOR EVALUATION OF SPECTRAL PROPERTIES OF A MEASUREMENT OBJECT

(71) Applicants: Reinhard März, München (DE); Gustav Müller, Osterhofen (DE)

(72) Inventors: Reinhard März, München (DE); Gustav Müller, Osterhofen (DE)

(*) Notice: Subject to any disclaimer, the term of this patent is extended or adjusted under 35 U.S.C. 154(b) by 53 days.

(21) Appl. No.: 15/953,895

(22) Filed: Apr. 16, 2018

(65) Prior Publication Data

US 2019/0316964 A1  Oct. 17, 2019

(51) Int. Cl.
*G01J 3/28* (2006.01)
*G01J 3/24* (2006.01)
*G01N 21/3563* (2014.01)
*G01J 3/10* (2006.01)

(52) U.S. Cl.
CPC .............. *G01J 3/24* (2013.01); *G01J 3/108* (2013.01); *G01J 3/2803* (2013.01); *G01N 21/3563* (2013.01); *G01J 2003/102* (2013.01); *G01N 2201/0627* (2013.01)

(58) Field of Classification Search
CPC .... G01J 3/02; G01J 3/18; G01J 3/2803; G01J 3/2823; G01J 3/28
USPC ...................................................... 356/328
See application file for complete search history.

(56) References Cited

U.S. PATENT DOCUMENTS

2006/0215955 A1* 9/2006 Mitamura ............ G02B 6/2931
                                                          385/18
2010/0034498 A1* 2/2010 Komiya ............... G02B 6/2931
                                                          385/18

* cited by examiner

*Primary Examiner* — Md M Rahman
(74) *Attorney, Agent, or Firm* — Maginot, Moore & Beck, LLP

(57) ABSTRACT

The invention relates to an apparatus and a method for evaluating spectral properties of a measurement object. It comprises a plurality of light emission units, each emitting light with a predetermined emission spectrum and having a respective output configured for emitting the light with the predetermined emission spectrum onto the measurement object, an optical spectrograph having an input port adapted to receive light from the measurement object and a diffraction unit adapted to distribute different wavelengths of the received light to different output ports comprising the optical detectors, wherein the diffraction unit is adapted to distribute said received light to the respective output ports such that the lights in the respective output port have different wavelengths at different diffraction orders; a signal identification unit adapted to identify which of the light emission units contribute to the respective light in the respective output ports.

18 Claims, 7 Drawing Sheets

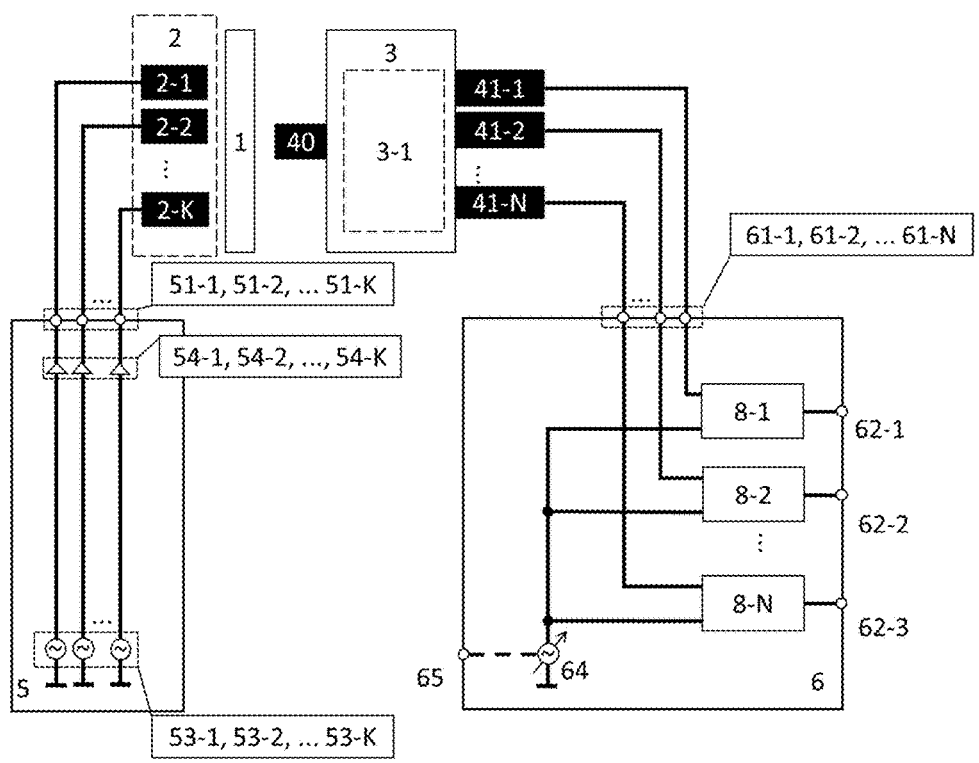
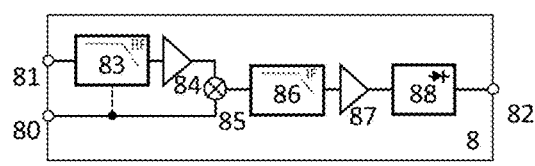
Fig. 5
Fig. 6

APPARATUS AND METHOD FOR EVALUATION OF SPECTRAL PROPERTIES OF A MEASUREMENT OBJECT

FIELD

The invention relates to spectroscopy, and more particularly to an apparatus and a method using a spectrograph with a plurality of light emission units operated sequentially or simultaneously to extend the spectral range of the spectrograph at a given spectral resolution.

BACKGROUND

One goal of optical spectroscopy is to determine the spectral content of electromagnetic radiation after it has interacted with some material or sample of interest. Typical wavelength dependent interactions include reflection, scattering and absorption and transmission.

Common instruments in the prior art fall into two general classes: spectrographs and spectrometers. A spectrograph disperses a spectrum in one step and records it using a multichannel optical detector, e.g. a photodiode array or a CCD camera. A spectrometer, in contrast, scans the spectrum mechanically or electronically and records the response sequentially using a single optical detector (D. W. Ball, "Field Guide to Spectroscopy", SPIE Press, 2006).

Realizations of spectrographs typically comprise dispersive elements, e.g. prisms, reflection or transmission gratings, or arrayed waveguide gratings. Current realizations of spectrometers are usually based on the superposition of light, e.g. by using Michelson-, Fabry-Perot-, or Mach-Zehnder couplers or interferometers.

Current advanced spectrometers can separate several 1000 channels with a spectral resolution in the order of 1 nm. Fourier transform infrared spectrometers (FT-IR) based on Michelson interferometers relax the requirements on the dimensions of the entrance slits and therefore achieve higher output signals (Jacquinot principle). In order to further increase the signal-to-noise ratio, multiple scans are employed (Fellgett principle). The spectral resolution, however, is related to the optical path difference and thus to the span of the moving mirror. Thus, the mechanical stability and the reliability of high-resolution instruments represent an important cost-factor which restricts the application of FT-TR spectrometers to high-end laboratory equipment. In addition, due to the sequential measurement mode, they suffer from measurement periods in the order of minutes for high-resolution spectra.

The measurement period of spectrographs, in contrast, is only limited by the response time of the multichannel optical detector and the subsequent electronic circuitry. Many spectrographs are mechanically robust since they do not exhibit any moving parts. Generally, their spectral resolution is limited by the number of equally spaced wavelength channels. Although this is not a physical limit, shifting it causes rapidly increasing technical difficulties and costs. Furthermore, compared to FT-IR spectrometers, spectrographs are more sensitive to the thermal noise of the detectors.

OBJECTS OF THE INVENTION

Therefore, the object of the present invention is to provide an apparatus and a method which circumvent the above described disadvantages, in particular measurement periods in the order of minutes for FT-IR spectrometers and the limited spectral resolution of conventional spectrographs.

SUMMARY OF THE DISCLOSURE

The invention according to one aspect provides an measurement apparatus for evaluating spectral properties of a measurement object, comprising a plurality of light emission units, each emitting light with a predetermined emission spectrum and having a respective output configured for emitting the light with the predetermined emission spectrum onto the measurement object, an optical spectrograph having an input port adapted to receive light from the measurement object and a diffraction unit adapted to distribute different wavelengths of received light to different output ports comprising the optical detectors, wherein the diffraction unit is adapted to distribute said received light to the respective output ports such that the lights in the respective output port have different wavelengths at different diffraction orders, and a signal identification unit adapted to identify which of the light emission units contribute to the respective light in the respective output ports.

The invention according to another aspect provides a method for evaluating spectral properties of a measurement object, comprising the following steps: emitting, by a plurality of light emission units, lights with predetermined emission spectra onto the measurement object, directing, the lights from the measurement object onto an optical spectrograph, distributing, by an optical spectrograph having a diffraction unit, different wavelengths of the light received from the measurement object to different output ports such that the lights in the respective output port have different wavelengths at different diffraction orders, and detecting, by optical detectors at the output ports, the lights, identifying, by a signal identification unit, which of the light emission units contribute to the respective light in the respective output ports.

Briefly summarizing, the improvements listed under "SOLUTION OF THE INVENTION" for the solution of the single object listed under "OBJECT OF THE INVENTION" let a N-channel spectrograph with K light emission units in fully simultaneous measurement mode work as an effective K*N spectrograph. Advantages of the inventive device (and correspondingly the method) are that it

- has the same size as a spectrograph with N channels;
- has the same measurement speed as a spectrograph with N channels;
- allows varying the channel positions and bandwidths over the spectral range to match the requirements of the targeted application;
- offers an excellent signal-to-noise ratio;
- is more cost-effective than conventional solutions as long as the optical setup dominates the device cost; and
- is mechanically more robust than conventional solutions.

Further advantageous embodiments and improvements of the invention are listed in the dependent claims. However, before coming to a detailed description of the embodiments of the invention with reference to the drawings, hereinafter some more general further aspects of the invention are considered.

According to a particularly advantageous aspect, the apparatus comprises a control unit adapted to control the plurality of light emission units to emit light onto the measurement object sequentially in time. This has the particular advantage that the cost of electronic circuitry is minimized.

According to another aspect, the apparatus comprises a control unit adapted to control the plurality of light emission units to emit light onto the measurement object simultaneously in time. This has the further advantage that the measurement period is minimized.

According to another aspect, the signal identification unit is a N-channel heterodyne receiver. This has the further advantage that the control unit and the signal identification unit are completely decoupled.

According to another aspect, the apparatus comprises light emitting units adapted to emit light in different wavelength ranges corresponding to the diffraction orders of the diffraction unit. This has the further advantage of technical ease and of optimum use of the apparatus. Furthermore, this aspect allows the use of a single AWG (Arrayed Waveguide Grating) in different wavelength regions thus reducing manufacturing costs.

According to yet another aspect, the diffraction unit can be an arrayed waveguide grating. This has the further advantage that arrayed waveguide gratings can easily be operated in high diffraction orders.

According to another aspect, the light emitting units can be one or more selected from the group consisting of a LED (Light Emitting Diode), an IRED (InfraRed Emitting Diode), a RCLED (Resonant Cavity Light Emitting Diode), an ELED (Edge Emitting LED), an SLED (Superluminescent LED), a semiconductor laser and a VCSEL (Vertical Cavity Surface Emitting Laser). This has the further advantage of using the optimal element with respect to small footprint, low power consumption and low cost in every wavelength region.

According to another aspect, the light identification unit comprises a plurality of amplifiers. This has the further advantage that the measurement period is minimized.

According to another aspect, the apparatus comprises one or more amplifiers selected from the group consisting of lock-in amplifier, boxcar amplifier and correlator. This has the further advantage that the signal-to-noise ratio is maximized.

According to another aspect, the light emitting units can emit light in the near infrared region. This has the further advantage that the apparatus can be used for chemometrics.

According to a particularly advantageous aspect, in the above method, the light beams from the plurality of light emission units can be emitted onto the measurement object sequentially in time. This has the particular advantage that the cost of electronic circuitry is minimized.

According to yet another aspect, in the above method, the lights from the plurality of light emission units are emitted onto the measurement object simultaneously in time. This has the further advantage that the measurement period is minimized.

According to another aspect, in the above method, the amplification is done by using a lock-in amplifier. This has the further advantage that the signal-to-noise ratio is maximized.

According to another aspect, in the above method, the lights from the plurality of light emission units are emitted in different wavelength ranges corresponding to the diffraction orders of the diffraction unit. This has the further advantage that at least one part of the hardware of the apparatus is shared.

According to another aspect, in the above method, the lights of the light emitting units are emitted in the near infrared region. This has the further advantage that the method can be used for chemometrics.

In addition, the invention according to another aspect provides an measurement apparatus for evaluating spectral properties of a measurement object, comprising a light emission unit adapted to emit light with a predetermined emission spectrum and having a respective output configured for emitting the light with the predetermined emission spectrum onto the measurement object, an optical spectrograph having an input port adapted to receive light from the measurement object and a diffraction unit adapted to distribute different wavelengths of the received light to different output ports comprising optical detectors, wherein the diffraction unit adapted to distribute said received light to the respective output ports in different wavelengths and diffraction orders.

In addition, the invention according to yet another aspect provides a method for evaluating spectral properties of a measurement object, comprising the following steps: emitting, by a light emission unit, light with a predetermined emission spectrum onto the measurement object, directing), the light from the measurement object onto an optical spectrograph, distributing, by the optical spectrograph having a diffraction unit, said received light to respective output ports of the spectrograph in different wavelengths and diffraction orders, detecting, by optical detectors at the output ports, the lights, identifying, by a signal identification unit the emitted light in the output ports.

Even when only one emission unit is used, the advantage of the inventive device and method is that it respectively
  allows for channel positions of the emission unit in adjacent diffraction orders;
  offers an excellent signal-to-noise ratio;
  is more cost-effective than conventional solutions as long as the optical setup dominates the device cost; and
  is mechanically more robust than conventional solutions.

Hereinafter, the invention will be described with reference to its advantageous embodiments with reference to the drawings. These drawings, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

BRIEF DESCRIPTION OF THE DRAWINGS

In the drawings:

FIG. 5 shows a realization of the apparatus using N-channel heterodyne detection;

FIG. 6 shows the parts of a heterodyne detection unit used in the apparatus in FIG. 5;

Figure 1:
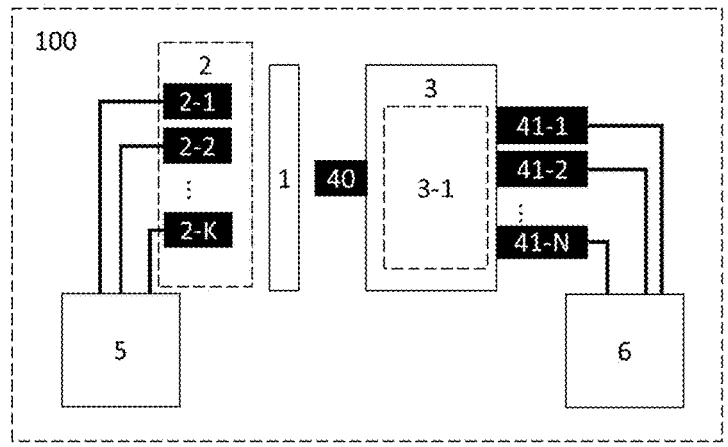
FIG. 1 is a block diagram of a first embodiment of the apparatus according to the invention.

Skilled artisans will appreciate that elements in the figures are illustrated for simplicity and clarity and have not necessarily been drawn to scale. For example, the dimensions and locations of some of the elements in the figures may be exaggerated relative to other elements to help improve understanding of embodiments of the present invention. The arrangement and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION

Briefly summarizing, as further explained below, the principle of the present invention is to extend the spectral range of a known spectrograph at a given spectral resolution by using one or a plurality of emission units with different emission spectra and by operating the spectrograph in a plurality of diffraction orders.

Before explaining the disclosed embodiments of the invention in detail, it is to be understood that the invention is not limited in its application to the details of the particular arrangement, since the invention is capable of other embodiments. Also, the terminology used herein is for the purpose of description and not of limitation.

FIG. 1 shows a block diagram of an embodiment of the apparatus 100 according to the invention for evaluating spectral properties of a measurement object 1. As shown in FIG. 1, the apparatus 100 comprises a plurality of light emission units 2-1, 2-2, . . . 2-K each emitting light with a predetermined emission spectrum and having a respective output configured for emitting the light with the predetermined emission spectrum onto a measurement object 1. An optical spectrograph 3 has an input port 40 adapted to receive light from the measurement object 1 and a diffraction unit 3-1 adapted to distribute different wavelengths of the received light to different output ports 41-1, 41-2, . . . 41-N comprising optical detectors. The light received from the measurement object 1 may be transmitted or reflected light. Reference numeral 5 designates a control unit for controlling the light emitting units, for example to modulate them.

The diffraction unit 3-1 is adapted to distribute the received light to the respective output ports 41-1, 41-2, . . . 41-N such that the lights in the respective output port have different wavelengths at different diffraction orders. In embodiments of the present invention, K=2 and N=3 (see the example below). Further preferably, for further typical working examples N=2 to 10 and K=8 to 128. However, it should be understood that the invention is by means limited to these numbers. Generally, N can be greater than K, N can be smaller than K or K can be equal to N, depending on the desired application. Hence, the number of N and K will depend on the desired application.

Figure 14:
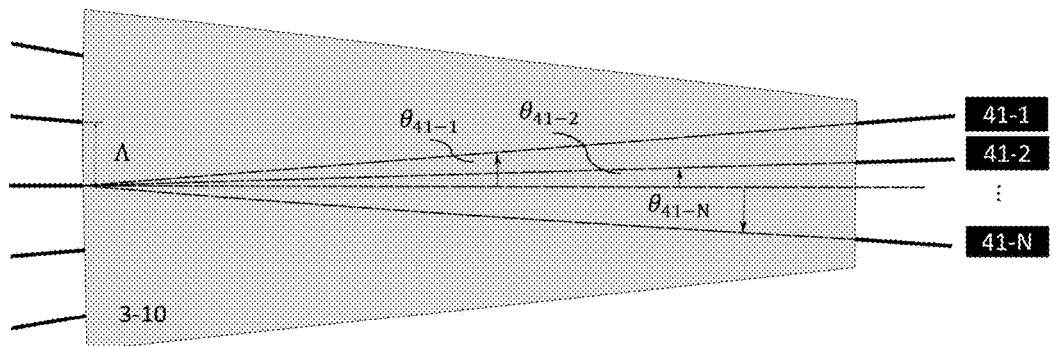
FIG. 14 illustrates the interdependence of wavelength and diffraction order for an optical phased array.

The feature that the lights in the respective output port have different wavelengths at different diffraction orders can be understood from the following principles of physics. The interdependence between a wavelength $\lambda$ and a diffraction order $m$ is governed by the grating equation $$d_{in} + \Lambda \sin \theta = m\lambda$$

which dates back to J. Fraunhofer, "Kurzer Bericht von den Resultaten neuerer Versuche über die Gesetze des Lichtes und die Theorie derselben," Ann. d. Phys. 74, 337-378 (1823). FIG. 14 illustrates the application to an arrayed waveguide grating. The diffraction region is a slab waveguide 3-10 in front of the output ports 41-1, 41-2, . . . 41-N, $\Lambda$ is the grating constant and $d_{in}$ is the optical path difference of the lights of adjacent incoming channel waveguides. The diffraction angle $\theta_{41\text{-}1}$ designates the angle between the center and the output port 41-1. Accordingly, the diffraction angles $\theta_{41\text{-}1}, \theta_{41\text{-}2}, \ldots \theta_{41\text{-}N}$ point to the output ports 41-1, 41-2, . . . 41-N. For the diffraction order m, lights with the wavelengths $\lambda_{m,41\text{-}1}, \lambda_{m,41\text{-}2}, \ldots \lambda_{m,41\text{-}N}$ will be directed to the output ports 41-1, 41-2, . . . 41-N.

For two different diffraction orders l and m, the wavelengths of the lights directed to the output ports 41-1, 41-2, . . . 41-N are then related by the following equations which can be derived from the grating equation, if the dispersion is neglected:

$$l\lambda_{l,41\text{-}1} = m\lambda_{m,41\text{-}1}$$

$$l\lambda_{l,41\text{-}2} = m\lambda_{m,41\text{-}2}$$

$$l\lambda_{l,41\text{-}N} = m\lambda_{m,41\text{-}N}$$

These features let a N-channel spectrograph with K light emission units mapped to the diffraction orders work as an effective K*N spectrograph. The inventive apparatus advantageously uses spectrographs which can work in high diffraction orders such as arrayed waveguide gratings (AWGs). It has the same size as a spectrograph with N channels. The apparatus is clearly more cost-effective and also mechanically more robust than conventional solutions.

Figure 7:
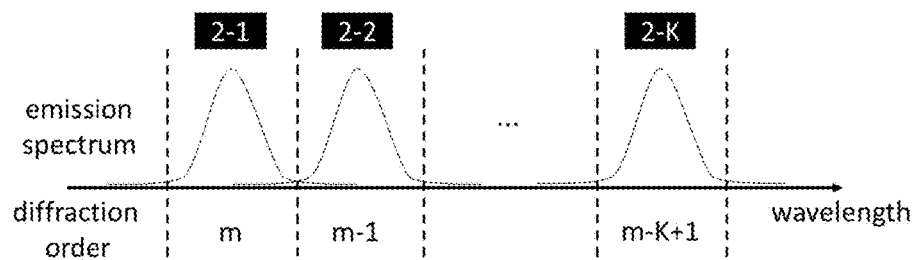
FIG. 7 shows the spectra of the emission units and optimum mapping to the corresponding diffraction orders (wavelengths not to scale of the apparatus according to the invention.

A simple numerical example with K=2 light emission units and N=3 output ports illustrates the operation of the inventive apparatus. In this example, the center wavelength of the first light emission unit is 1500 nm and the arrayed waveguide grating works in the $31^{st}$ diffraction order for this light emission unit. The center wavelength of the second light emission unit is 1550 nm and the arrayed waveguide grating will, according to the above equations, work in the $30^{th}$ diffraction order for this light emission unit. If the spectral widths of the light emission units are below 50 nm, light from the first emission unit will only exist in $31^{st}$ diffraction order and light from the second emission unit will only exist in $30^{st}$ diffraction order as shown in FIG. 7. If the arrayed waveguide grating is constructed such that the wavelengths assigned to the output ports 41-1, 41-2 and 41-3 are for the first emission unit 1480 nm, 1500 nm, 1520 nm, the wavelengths assigned to the output ports 41-1, 41-2 and 4-3 will, according to the above equations, be for the second emission unit 1529.3 nm, 1550 nm, 1570.6 nm, i.e. the light at the output port 41-1 has a wavelength of 1480 nm from the or relating to the first emission unit and 1529.3 nm from the or relating to the second emission unit. Light at the output port 41-2 has a wavelength of 1500 nm from the or relating to the first emission unit and 1550 nm from the or relating to the second emission unit. Light at the output port 41-3 has a wavelength of 1520 nm from the or relating to the first emission unit and 1570.6 nm from the or relating to the second emission unit.

Hence, this example illustrates what is meant by "such that the lights in the respective output port have different wavelengths at different diffraction orders", namely that each output port has a light contribution from each light emission unit (in the above example each of the three output ports 41-1, 41-2, 41-3 has two lights (light contributions or light parts) from two light emission units). However, the light contributions per port are not in the same diffraction order in the respective port (in the above example, the two lights in the respective output port are in the 31$^{st}$ diffraction order (for the first emission unit) and in the 30$^{th}$ diffraction order (for the second emission unit)). On the other hand, the different diffraction orders per output port are the same in each output port, that is each output port has the light contribution from the first emission unit and the second light emission unit in the same (different) diffraction order, however, at respective different wavelengths. An AWG as described here as one embodiment of the diffraction unit 3-1 is capable of producing the light contributions at the respective output ports at different wavelengths and in the different orders as just explained. Hence, whilst in classical spectroscopy higher order lights produced by gratings were considered as degradation and consequently were not used, in the present invention it is the particular desire to exploit and use these higher order lights for spectroscopy.

The apparatus 100 in FIG. 1 further comprises a signal identification unit 6 adapted to identify which of the light emission units contribute to the respective light in the respective output ports. This signal identification unit 6 is provided for two reasons. Firstly, the signal-to-noise ratio of the measured spectra can be improved if a light emission unit is modulated. Secondly, by modulating the light emission units 2-1, 2-2, . . . 2-K individually, for example by the control unit 5, it becomes possible to identify each single emission unit by an analysis of the lights of the output ports 41-1, 41-2, . . . 41-N. Having the light emission units at the input modulated by the control unit 5 thus allows the signal identification unit 6 at the output to identify, when looking at the output light, the origin of the light, i.e. from which light emission unit the light stems.

The apparatus 100 including the N-channel spectrograph shown in FIG. 1 preferably has a fully simultaneous measurement mode in which it works as an effective K*N spectrograph. This has the advantage that at least a part of the hardware of the apparatus is shared.

Figure 11:
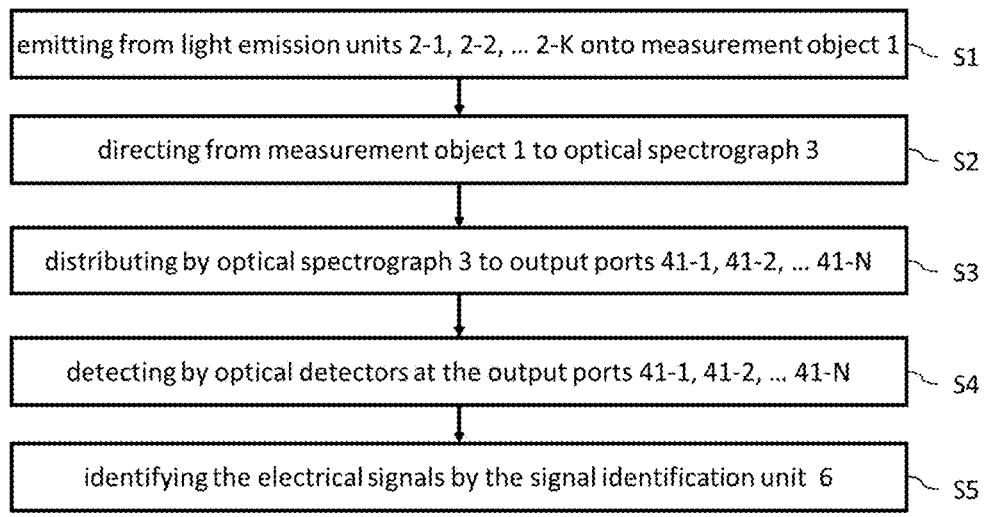
FIG. 11 shows a flow diagram of a first embodiment of the method according to the invention.

With reference to FIG. 1, FIG. 11 shows an embodiment of the inventive method for evaluating spectral properties of the measurement object 1. As shown in FIG. 11, there is a first step S1 in which a plurality of light emission units 2-1, 2-2, . . . 2-K emit lights with predetermined emission spectra onto the measurement object 1. In a second step S2, the lights from the measurement object 1 are directed to the optical spectrograph 3. In a further step S3 the optical spectrograph having a diffraction unit 3-1 of FIG. 1 distributes different wavelengths of the light received (transmitted or reflected) from the measurement object 1 to different output ports 41-1, 41-2, . . . 41-N such that the lights in the respective output port have different wavelengths at different diffraction orders. In step S4 the optical detectors detect the lights at the output ports 41-1, 41-2, . . . 41-N. In step S5, the signal identification unit 6 identifies the lights from the light emission units 2-1, 2-2, . . . 2-K based on an analysis of the signals of the output ports 41-1, 41-2, . . . 41-N.

Although the high-priced part of the hardware of the apparatus 100 shown in FIG. 1—spectrograph and detector array—is shared between a plurality of spectral ranges, the methodology allows an identification of the channels controlled by the light emission units.

Figure 2:
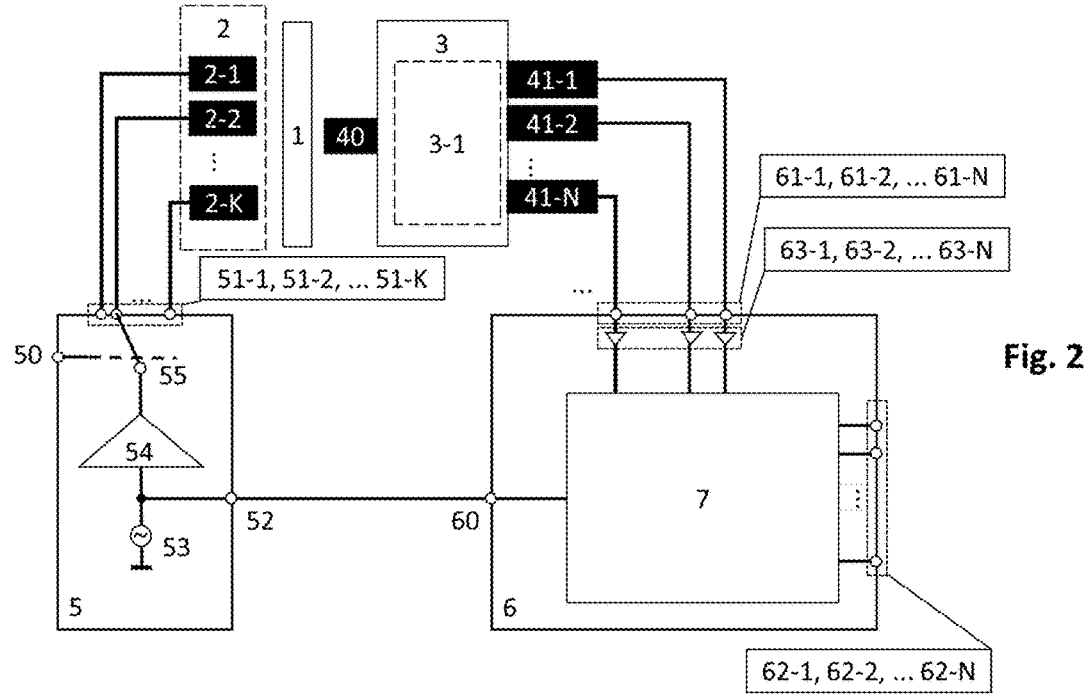
FIG. 2 shows a realization of the apparatus using lock-in amplifiers.

FIG. 2 shows a block diagram of the apparatus 100 comprising a control unit 5 adapted to control the plurality of light emission units 2-1, 2-2, . . . 2-K to emit light onto the measurement object 1 sequentially in time. This has the particular advantage that the cost of the apparatus is minimized.

The block diagram in FIG. 2 illustrates an embodiment based on lock-in amplifiers. The control unit 5 comprises an input port 50 to drive a 1:K switch 55 selecting the output ports 51-1, 51-2, . . . 51-K of the control unit 5 driving the light emission units 2-1, 2-2, . . . 2-K sequentially. The lock-in implementation further comprises a signal generator 53, the corresponding output port 52, and an amplifier 54.

Figure 3:
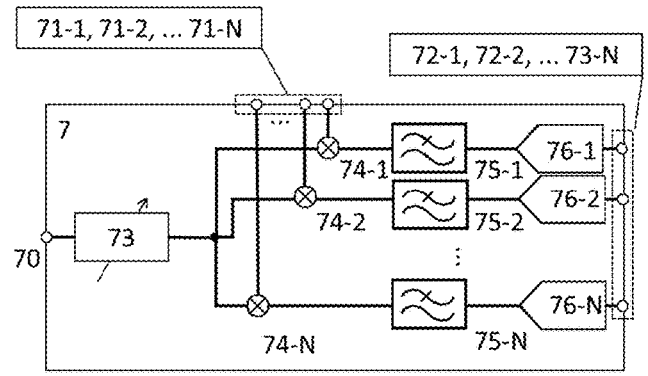
FIG. 3 shows the parts of the N-channel detection unit.

The signal identification unit 6 can comprise an N-channel detection unit 7, as shown in detail in FIG. 3. An input port 60 for a reference signal is connected to the corresponding port 52 of the control unit 5. The analog input port of the N-channel detection unit 7 is, after pre-amplification using amplifiers 63-1, 63-2, . . . 63-N, connected to the corresponding output ports 61-1, 61-2, . . . 61-N of the signal identification unit 6. The N-channel detection unit 7 is connected to the digital output ports 62-1, 62-2, . . . 62-N.

Figure 4:
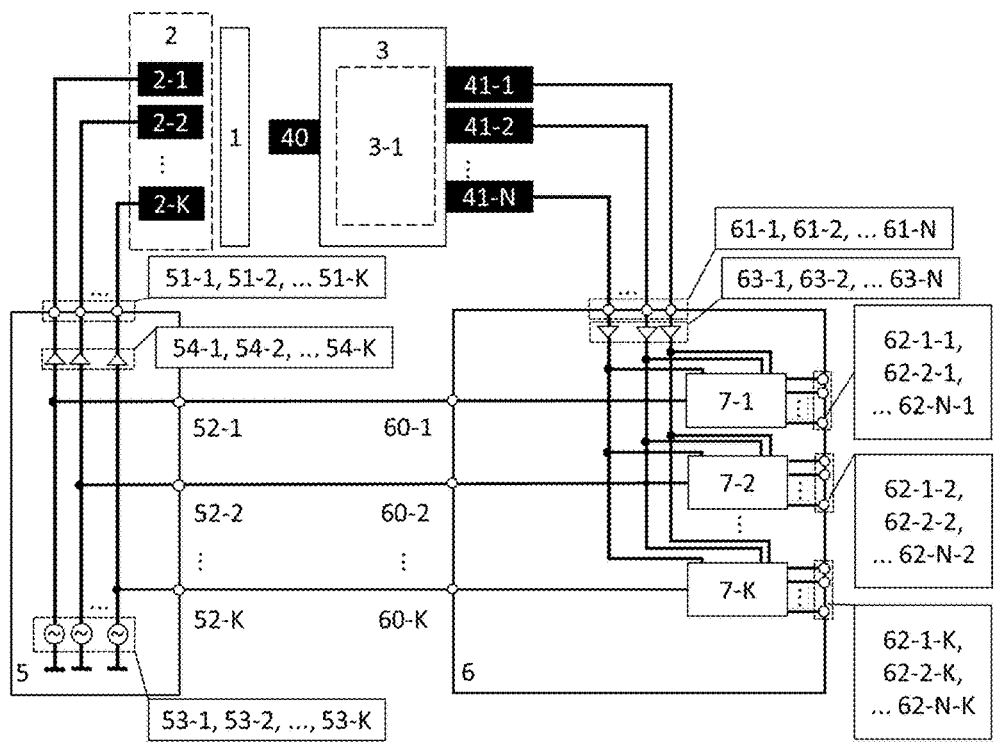
FIG. 4 shows another realization of the apparatus of the invention using lock-in amplifiers.

FIG. 3 shows further details of the N-channel detection unit 7 used in the implementations described in FIG. 2 and FIG. 4. Reference numeral 70 designates an input port for the reference signal, reference numerals 71-1, 71-2, . . . 71-N designate the analog input ports of the N-channel detection unit, reference numerals 72-1, 72-2, . . . 72-N designate the digital output ports. Reference numeral 73 designates a delay element, reference numerals 74-1, 74-2, . . . 74-N designate mixers. Reference numerals 75-1, 75-2, . . . 75-N designate low-pass filters and reference numerals 76-1, 76-2, . . . 76-N designate analog-to-digital converters. Optional electronic functions such as bandpass filters, notch filters, analog signal compressors, e.g. logarithmic amplifiers, automatic gain control or range switching, and output amplifiers are not shown.

As a modification of the of the N-channel detection unit according to FIG. 3, the single delay element 73 shown in FIG. 3, can be replaced by N individually tunable delay elements, each one located in an input line in front of a mixer 74-1, 74-2, . . . 74-N. Such a setup is useful for time-resolved measurements.

FIG. 4 shows another embodiment of the apparatus 100, comprising a control unit 5 adapted to control the plurality of light emission units 2-1, 2-2, . . . 2-K to emit light onto the measurement object 1 simultaneously in time. It also illustrates an aspect of the method according to the invention, wherein the lights from the plurality of light emission units 2-2, 2-1, . . . 2-K are emitted onto the measurement object 1 simultaneously in time.

FIG. 4 shows a specific embodiment of the invention based on lock-in amplifiers. In this embodiment, the control unit 5 comprises output ports 51-1, 51-2, . . . 51-K driving the light emission units 2-1, 2-2, . . . 2-K simultaneously by using signal generators 53-1, 53-2, . . . 53-K amplified separately by the amplifiers 54-1, 54-2, . . . 54-K, and output ports for reference signals 52-1, 52-2, . . . 52-K.

In FIG. 4, the signal identification unit 6 can comprise K N-channel detection units 7-1, 7-2, . . . 7-K whose input ports for the reference signals 60-1, 60-2, . . . 60-K are connected to the corresponding ports 52-1, 52-2, . . . 52-K. After pre-amplification using the amplifiers 63-1, 63-2, . . . 63-N, the analog input ports 71-1, 71-2, . . . 71-N of the N-channel detection units 7-1, 7-2, . . . 7-K are connected to the corresponding ports 61-1, 61-2, . . . 61-N of the signal identification unit 6. Each of the N-channel detection units 7-1, 7-2, . . . 7-K has separate digital output ports, i.e. the N-channel detection unit k is connected to the digital output ports 62-k-1, 62-k-2, . . . 62-k-N where k is any number between 1 and K.

FIG. 5 shows a further embodiment of the apparatus of the invention. In FIG. 5 the apparatus 200 EINZEICHNEN includes a control unit 5 comprising output ports 51-1, 51-2, . . . , 51-K driving the light emission units 2-1, 2-2, . . . 2-K simultaneously by using signal generators 53-1, 53-2, . . . 53-K amplified separately by the amplifiers 54-1, 54-2, . . . 54-K. The signal identification unit 6 comprises a plurality of heterodyne detection units 8-1, 8-2, . . . 8-N connected to the corresponding ports 61-1, 61-2, . . . 61-N of the signal identification unit 6. The heterodyne detection units 8-1, 8-2, . . . 8-N share a local oscillator 64 which can be tuned via port 65. One advantage of the configuration according to FIG. 5 is that the control unit 5 and the signal identification unit 6 are completely decoupled.

FIG. 6 shows a standard realization of the heterodyne detection unit 8 used in the implementation shown in FIG. 5. In FIG. 6, reference numeral 80 designates the input port of the reference from the local oscillator 64, numeral 81 the input port from the signals emitted from one of the light emission units 2-1, 2-2, . . . 2-K. The signal from port 81 is first filtered by a "radio" frequency RF band-pass filter 83, i.e. the signal used by one of the signal generators 53-1, 53-2, . . . 53-K in the control unit 5. The dotted line indicates that the local oscillator and RF filter 83 are tuned in tandem. Next the signal passes the RF amplifier 84. The frequency mixer 85 carries out the actual heterodyning, i.e. it changes the incoming radio frequency signal to a fixed intermediate frequency IF. The signal then passes the IF band-pass filter 86, the optional IF amplifier 87, and the demodulator 88.

FIG. 7 shows preferred spectra of the emission units and optimal mapping to the corresponding diffraction orders in the embodiments of the invention. Wavelengths are not to scale. In particular, in order to allow the lights to be distributed by the diffraction unit to the different output ports such that the lights in the respective output port have different wavelengths at different diffraction orders, each light emitting unit 2-1, 2-2 . . . 2-K has a spectral width substantially limited to the respective diffraction order m, m−1 . . . m−K+1 wavelength.

Figure 8:
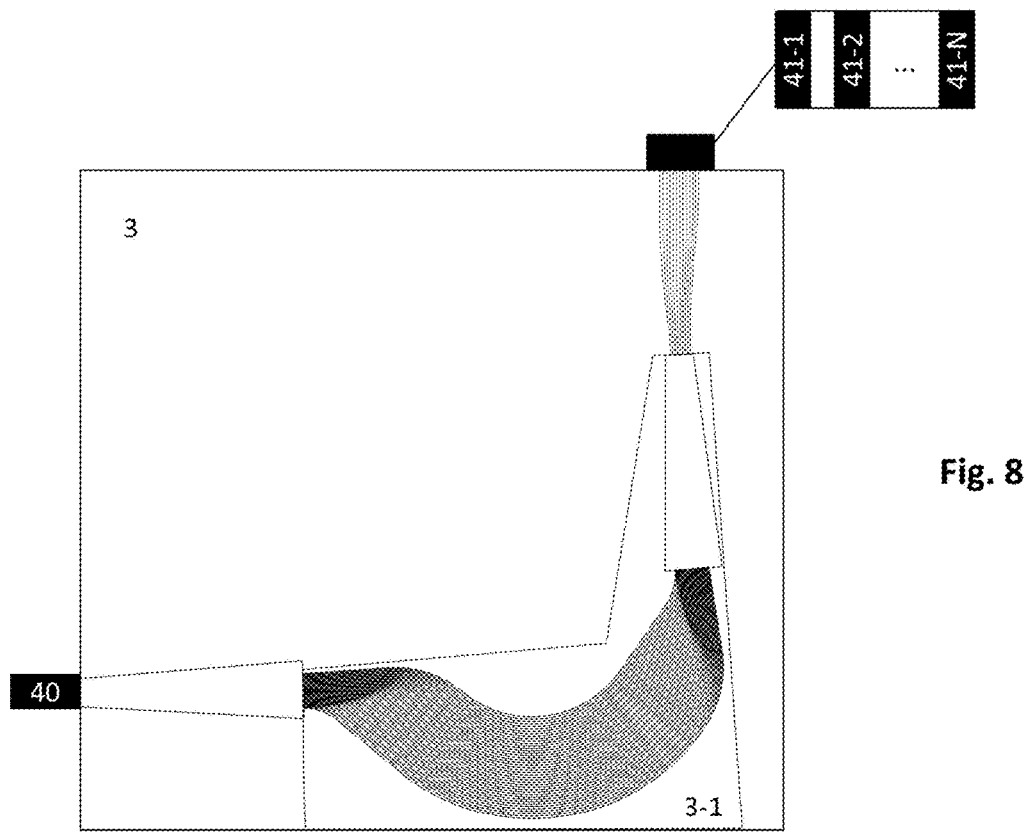
FIG. 8 shows an optical spectrograph based on an arrayed waveguide grating according to the invention.

FIG. 8 shows an embodiment of the apparatus of the invention where the diffraction unit 3-1 is an arrayed waveguide grating (AWG). The diffraction region is a slab waveguide 3-10 in front of the output ports 41-1, 41-2, . . . 41-N. Arrayed waveguide gratings are optimized for operation in high diffraction order.

In general, the light emitting units 2-1, 2-2, . . . 2-K can be selected from the group consisting of an LED, an IRED, a RCLED, an ELED, an SLED, a semiconductor laser and a VCSEL which offer a plurality of advantages including the option to transmit required signals to the signal identification unit, to provide an emission spectrum compatible with the spectrograph, and to offer small size and low power consumption compared to usual broadband emission units.

Figure 9:
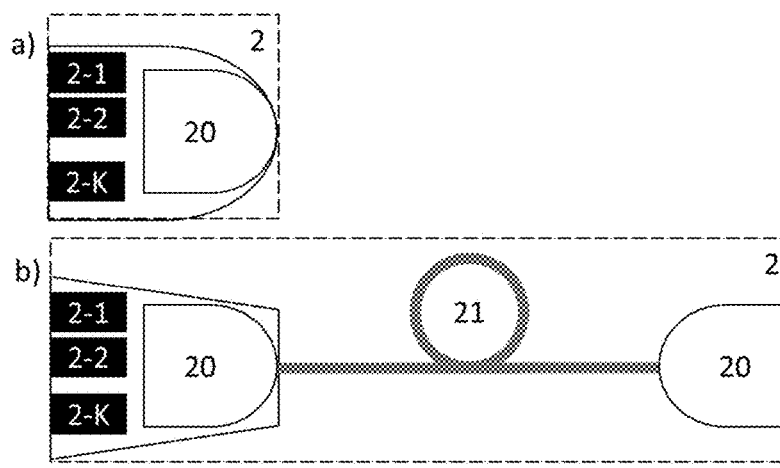
FIG. 9 shows arrangements of the emission units without (a) and with fiber pigtail, (b) and (c)

FIG. 9 shows optional arrangements of the emission units 2: without fiber pigtail in FIG. 9a and with fiber pigtail in FIG. 9b and FIG. 9c. According to FIG. 9a, the apparatus can comprise a light emitting unit 2 comprising a lens 20 for collimating the lights of the light emission units 2-1, 2-2, . . . 2-K and directing them to the measurement object 1. According to FIG. 9b, the apparatus can comprise a light emitting unit 2 comprising a lens 20 coupling the lights of light emission units 2-1, 2-2, . . . 2-K into an optical fiber 21 and directing them via a second lens to the measurement object 1. According to FIG. 9c a setup can be used where the lights of the emission units 2-1, 2-2, . . . 2-K of the light emitting unit 2 are separately coupled to optical fibers which in turn are coupled into a single optical fiber 21 using an optical multiplexer 22 and then directed via a second lens 20 to the measurement object 1. Arrangements with fiber pigtail are preferred when either the access to the measurement object 1 is complicated or measurements are done in an explosive environment.

For the arrangements according to FIGS. 9b and 9c, any kind of single-mode and multimode fibers can be used and best practice is to adapt the fiber type to the requirements of the spectrograph.

Figure 10:
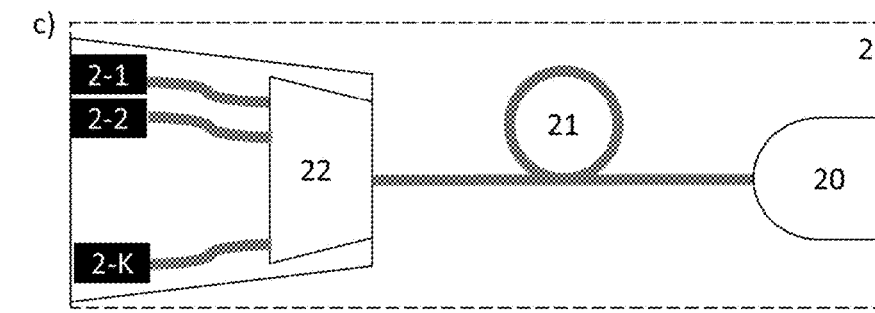
FIG. 10 shows a realization of the input unit 40 of the spectrograph for reflection measurements.

FIG. 10 shows an embodiment of the input unit 40 of the spectrograph for reflection measurements shown in FIG. 1. It can comprise a collimation lens 401 coupling the lights into a fiber 402. An optical multiplexer 403 combines the lights of the emission units 2-1, 2-2, . . . 2-K according to FIG. 9b or 9c and the optical spectrograph 3. The optical path between optical multiplexer 403 and the measurement object 1 has to provide a high return loss to prevent light from traveling back. Arrangements with fiber pigtail are preferred when either the access to the measurement object is complicated or measurements are done in an explosive environment.

Figure 12:
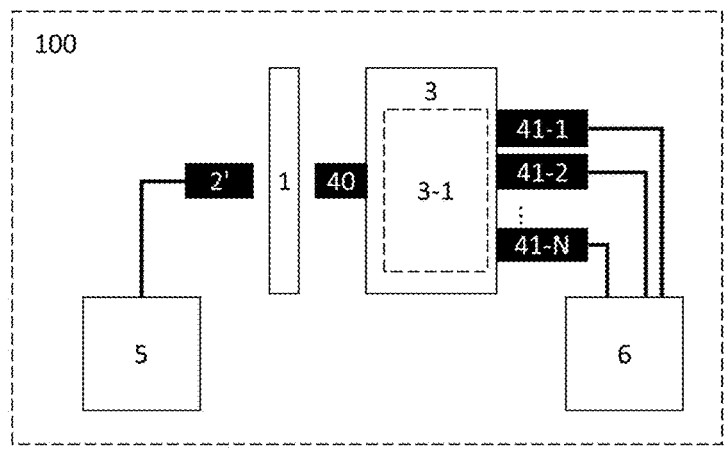
FIG. 12 is a block diagram of a second embodiment of the method according to the invention.

FIG. 12 shows a block diagram of a second embodiment of the apparatus according to the invention for evaluating spectral properties of a measurement object 1. As shown in FIG. 12, it comprises a single light emission unit 2' adapted to emit light with a predetermined emission spectrum and having a respective output configured for emitting the light with the predetermined emission spectrum onto the measurement object 1. An optical spectrograph 3 has an input port 40 adapted to receive light from the measurement object 1 and a diffraction unit 3-1 adapted to distribute different wavelengths of the received light to different output ports 41-1, 41-2, . . . 41-N comprising the optical detectors. The diffraction unit 3-1 distributes said received light to the respective output ports 41-1, 41-2, . . . 41-N in different wavelengths and diffraction orders. The light received from the measurement object 1 may be transmitted or reflected light.

Figure 13:
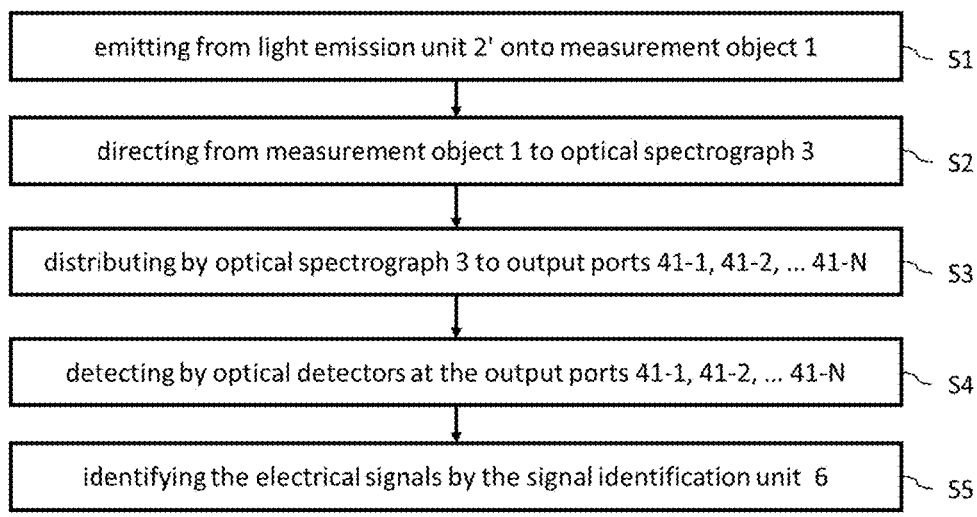
FIG. 13 shows a flow diagram of a further embodiment of the apparatus according to the invention.

With reference to FIG. 12, FIG. 13 shows a second embodiment of the inventive method for evaluating spectral properties of the measurement object 1. As shown in FIG. 13, there is a first step S1 in which a single light emission unit 2' emits light with a predetermined emission spectrum onto the measurement object 1. In a second step S2, the light from the measurement object 1 is directed onto an optical spectrograph 3. In a further step S3, the optical spectrograph 3 having a diffraction unit 3-1 of FIG. 12 distributes different wavelengths of the light received from the measurement object 1 to different output ports 41-1, 41-2, . . . 41-N such that the lights in the respective output port have different wavelengths at different diffraction orders. In step S4, the optical detectors detect the lights at the output ports 41-1, 41-2, . . . 41-N. In step S5, the signal identification unit 6 identifies the lights from the light emission units 2-1, 2-2, . . . 2-K based on an analysis of the signals of the output ports 41-1, 41-2, . . . 41-N.

The N-channel spectrograph shown in FIG. 11 preferably has only one emission unit.

Even, when only one emission unit is used as in the second embodiment, it still allows for channel positions of the emission unit in adjacent diffraction orders, i.e. the emission unit must not perfectly match the diffraction orders of the spectrograph.

From the current point of view, near-infrared spectroscopy is the most attractive application of the invention which can use light-emitting diodes LEDs in the NIR wavelength region. Such elements are available from several suppliers like Hamamatsu www.hamamatsu.com or LED Microsensor NT (www.lmsnt.com). For use in the UV, visible or IR wavelength regions, LEDs are available from suppliers like Nichia (www.nichia.co.jp), OSRAM (www.osram.com/cb/index.jsp), CRE E (www.cree.com/led-chips/products) or LED Microsensor NT (lmsnt.com/). Photodiodes in the NIR and IR regions, usable for the invention, are available in the market, e.g. from Hamamatsu (www.hamamatsu.com), LASER COMPONENTS (www.lasercomponents.com) or LED Microsensor NT lmsnt.com, Furthermore, for use in the invention, photodiodes for UV and visible applications based on Si and optimized for a special wavelength range are available from LASER COMPONENTS (www.lasercomponents.com).

Arrayed waveguide gratings, usable in the invention, are available from NTT Electronics (www.ntt-electronics.com) including devices with channel spacings of 25-200 GHz corresponding to 0.2-1.6 nm at 1550 nm and between 8 and 128 wavelength channels.

The invention may use lock-in amplifiers, boxcar amplifiers or correlators available as stand-alone devices, which have been available for many years. They may be used to serve as the signal identification unit as a system on chip (SoC).

One target application of the invention is spectroscopy. The near-infrared spectroscopy of the invention using the near-infrared region of the electromagnetic spectrum from 780 nm to 2500 nm is particularly useful for chemometrics including pharmaceutical, food and agrochemical quality control as well as for medical and physiological diagnostics and Mid-infrared spectroscopy from 2500 nm to 25000 nm. Due to its small size, low weight and fast processing speed the apparatus of the invention can be used advantageously as a small portable testing device for ad hoc tests of pharmaceutical substances such that the substances can be tested on site without the need to send samples thereof to an analysis lab, saving costs and time.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential feature or element of any or all the claims. The invention is defined solely by the appended claims including any amendments made during the pendency of this application and all equivalents of those claims as issued.

Moreover, in this document, relational terms such as first and second, top and bottom, and the like may be used solely to distinguish one entity or action from another entity or action without necessarily requiring or implying any actual such relationship or order between such entities or actions. The terms "comprises", "comprising", "has", "having", "includes", "including", "contains", "containing", or any other variation thereof, are intended to cover a non-exclusive inclusion, such that a process, method, article, or apparatus that comprises, has, includes, contains a list of elements does not include only those elements, but may include other elements not expressly listed or inherent to such process, method, article, or apparatus. An element proceeded by "comprises . . . a", "has . . . a", "includes . . . a", or "contains . . . a", does not, without more constraints, preclude the existence of additional identical elements in the process, method, article, or apparatus that comprises, has, includes, or contains the element. The terms "a" and "an" are defined as one or more unless explicitly stated otherwise herein. The terms "substantially", "essentially", "approximately", "about", or any other version thereof, are defined as being close to as understood by one of ordinary skill in the art, and in one non-limiting embodiment the term is defined to be within 10%, in another embodiment within 5%, in another embodiment within 1%, and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") such as microprocessors, digital signal processors, customized processors, and field programmable gate arrays (FPGAs), and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain functions are implemented as custom logic. Of course, a combination of the two approaches could be used.

Software programs containing software instructions for carrying out the functionalities and method steps in the described units may be used. Therefore, one or more embodiments can be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein, will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims.

In addition, in the foregoing description it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the description, with each claim standing on its own as a separately claimed subject matter.

1 measurement object
2 arrangement of the light emission units
2' light emission unit
2-1, 2-2, . . . 2-K light emission units
20 lens used in an arrangement of the light emission units
21 optical fiber used in an arrangement of the light emission units
22 optical fiber multiplexer used in an arrangement of the light emission units
3 optical spectrograph
3-1 diffraction unit
40 input port of the optical spectrograph
41-1, 41-2, . . . 41-N output ports of the optical spectrograph comprising optical detectors
5 control unit of the light emission units
50 input port of the control unit driving the 1:K switch
51-1, 51-2, . . . 51-K output ports of the control unit driving the light emission units
52-1, 52-2, . . . 52-K output ports of the control unit providing the reference signals
53-1, 53-2, . . . 53-K signal generators
54-1, 54-2, . . . 54-K amplifiers for the signal generators
6 signal identification unit
60 single input port of the signal identification unit for the reference signal
60-1, 60-2, . . . 60-K multiple input ports of the signal identification unit for the reference signal
61-1, 61-2, . . . 61-N input ports of the signal identification unit for the output ports of the spectrograph
62-1, 62-2, . . . 62-N output ports of the signal identification unit assigned to the output ports of the spectrograph
62-$k$-1, 62-$k$-2, . . . 62-$k$-N output ports of the signal identification unit assigned to the output ports of the spectrograph and the emission unit k
63-1, 63-2, . . . 63-N preamplifiers for the signals from the detectors
64 local oscillator
7 N-channel detection unit
7-1, 7-2, . . . 7-N multiple N-channel detection units
70 input port for the reference signal of a N-channel detection unit
71-1, 71-2, . . . 71-N analog input ports of a N-channel detection unit
72-1, 72-2, . . . 72-N digital output ports of a N-channel detection unit
73 delay element of a N-channel detection unit
74-1, 74-2, . . . 74-N mixers of a N-channel detection unit
75-1, 75-2, . . . 75-N low-pass filters of a N-channel detection unit
76-1, 76-2, . . . 76-N analog-to-digital converters of a N-channel detection unit
8 heterodyne detection unit
8-1, 8-2, . . . 8-N multiple heterodyne detection units
80 input port for the reference from the local oscillator
81 input port for the signal from one detector
82 output port of a heterodyne detection unit
83 radio frequency (RF) band-pass filter
84 amplifier for the signal from one detector
85 frequency mixer
86 intermediate frequency (IF) band-pass filter
87 amplifier for an intermediate frequency (IF) signal

The invention claimed is:

1. A measurement apparatus (100) for evaluating spectral properties of a measurement object (1); comprising:
a plurality of light emission units (2-1, 2-2, . . . 2-K), each emitting light with a predetermined emission spectrum and having a respective output configured for emitting the light with the predetermined emission spectrum onto the measurement object (1);
an optical spectrograph (3) having an input port (40) adapted to receive light from the measurement object (1) and a diffraction unit (3-1) adapted to distribute different wavelengths of the received light to different output ports (41-1, 41-2, . . . 41-N) comprising optical detectors;
the diffraction unit (3-1) adapted to distribute said received light to the respective output ports (41-1, 41-2, . . . 41-N) such that the lights in the respective output port have different wavelengths at different diffraction orders; and
a signal identification unit (6) adapted to identify which of the light emission units contribute to the respective light in the respective output ports.

2. The apparatus according to claim 1, further comprising a control unit (5) adapted to control the plurality of light emission units (2-1, 2-2, . . . 2-K) to emit light onto the measurement object (1) sequentially in time.

3. The apparatus according to claim 2, further comprising a control unit (5) adapted to control the plurality of light emission units (2-1, 2-2, . . . 2-K) to emit light onto the measurement object (1) simultaneously in time.

4. The apparatus according to claim 1, further comprising a control unit (5) adapted to control the plurality of light emission units (2-1, 2-2, . . . 2-K) to emit light onto the measurement object (1) simultaneously in time.

5. The apparatus according to claim 1, wherein the signal identification unit (6) is a N-channel heterodyne receiver.

6. The apparatus according to claim 1, wherein the light emitting units (2-1, 2-2, . . . 2-K) are adapted to emit light in respectively different wavelength ranges corresponding to the diffraction orders of the diffraction unit.

7. The apparatus according to claim 1, wherein said diffraction unit (3-1) is an arrayed waveguide grating.

8. The apparatus according to claim 1, wherein said light emitting units (2-1, 2-2, . . . 2-K) are one or more selected from the group consisting of a pumped broadband fiber source, a LED, a RED, a RCLED, a ELED, a SLED, a semiconductor laser and a VCSEL.

9. The apparatus according to claim 1, wherein said light identification unit (6) comprises a plurality of amplifiers.

10. The apparatus according to claim 9, wherein said amplifiers comprise one or more selected from the group consisting of a lock-in amplifier, a boxcar amplifier and a correlator.

11. The apparatus according to claim 1, wherein said light emitting units (2-1, 2-2, . . . 2-K) emit light in the near infrared region.

12. The method according to claim 1, wherein the lights of the light emitting units (2-1, 2-2, . . . 2-K) are in the near infrared region.

13. The method according to claim 1, wherein the lights of the light emitting units (2-1, 2-2, . . . 2-K) are in the near infrared region.

14. A method for evaluating spectral properties of a measurement object (1), comprising the following steps emitting (S1), by a plurality of light emission units (2-1, 2-2, . . . 2-K), lights with predetermined emission spectra onto the measurement object (1);

directing (S2), the lights from the measurement object (1) onto an optical spectrograph (3);

distributing (S3), by the optical spectrograph (3) having a diffraction unit (3-1), different wavelengths of the light received from the measurement object (1) to different output ports (41-1, 41-2, . . . 41-N) such that the lights in the respective output port have different wavelengths at different diffraction orders; and detecting (S4), by optical detectors at the output ports (41-1, 41-2, . . . 41-N), the lights; and identifying (S5), by a signal identification unit (6), which of the light emission units contribute to the respective light in the respective output ports.

15. The method according to claim 14, wherein the lights from the plurality of light emission units (2-2, 2-1, . . . 2-K) are emitted onto the measurement object (1) sequentially in time.

16. The method according to claim 14, wherein the lights from the plurality of light emission units (2-1, 2-2, . . . 2-K) is emitted onto the measurement object (1) simultaneously in time.

17. The method according to claim 14, wherein said identifying step comprises amplifying output signals of the optical detectors, wherein the amplification is done by using a lock-in amplifier.

18. The method according to claim 14, wherein the lights from the plurality of light emission units (2-1, 2-2, . . . 2-K) are emitted in different wavelength ranges corresponding to the diffraction orders of the diffraction unit (3-1).

\* \* \* \* \*